United States Patent
Chapman et al.

(10) Patent No.: US 10,238,056 B2
(45) Date of Patent: Mar. 26, 2019

(54) HIGH OLEIC SEED OIL TRAIT IN COTTON VARIETIES TO ELEVATE OLEIC ACID CONTENT OF COTTONSEED OIL

(71) Applicant: University of North Texas, Denton, TX (US)

(72) Inventors: Kent Chapman, Denton, TX (US); Patrick Horn, Holt, MI (US); Drew Sturtevant, Southlake, TX (US); Christopher Kennedy, Fort Worth, TX (US)

(73) Assignee: UNIVERSITY OF NORTH TEXAS, Denton, TX (US)

( * ) Notice: Subject to any disclaimer, the term of this patent is extended or adjusted under 35 U.S.C. 154(b) by 0 days.

(21) Appl. No.: 15/632,974

(22) Filed: Jun. 26, 2017

(65) Prior Publication Data

US 2017/0367293 A1 Dec. 28, 2017

Related U.S. Application Data

(60) Provisional application No. 62/355,064, filed on Jun. 27, 2016.

(51) Int. Cl.
| | |
|---|---|
| *A01H 5/10* | (2018.01) |
| *A01H 6/60* | (2018.01) |
| *C12Q 1/6895* | (2018.01) |
| *A01H 1/02* | (2006.01) |
| *A01H 1/04* | (2006.01) |
| *C12N 9/02* | (2006.01) |

(52) U.S. Cl.
CPC .............. *A01H 5/10* (2013.01); *A01H 1/02* (2013.01); *A01H 1/04* (2013.01); *A01H 6/604* (2018.05); *C12N 9/0071* (2013.01); *C12Q 1/6895* (2013.01); *C12Y 114/19* (2013.01); *C12Q 2600/13* (2013.01); *C12Q 2600/156* (2013.01)

(58) Field of Classification Search
None
See application file for complete search history.

(56) References Cited

PUBLICATIONS

Sturtevant et al, Planta, 2017, vol. 245, pp. 595-610 (Year: 2017).*
Shockey et al, Planta, 2017, vol. 245, pp. 611-622 (Year: 2017).*

* cited by examiner

*Primary Examiner* — Eileen B O Hara
(74) *Attorney, Agent, or Firm* — Jackson Walker LLP (57) ABSTRACT

An identified 90 bp sequence insertion in the GB0331 genome disrupts the coding sequence of the FAD2-1D gene near the 3' end of the protein coding region. This sequence is not found in reference genomes of other *Gossypium* species. This DNA segment can be used to track the high oleic fad-2-1D mutant allele for introgression into cotton varieties such as Pima and upland cotton varieties. This enables a non-GMO strategy to elevate the oleic acid content of commercial cottonseed oil.

14 Claims, 4 Drawing Sheets
Specification includes a Sequence Listing.

SEQUENCE LISTING

<160> NUMBER OF SEQ ID NOS: 11

<210> SEQ ID NO 1
<211> LENGTH: 1767
<212> TYPE: DNA
<213> ORGANISM: Gossypium barbadense (Accession GB0331)
<220> FEATURE:
<221> NAME/KEY: misc_feature
<222> LOCATION: (1727)..(1727)
<223> OTHER INFORMATION: n is a, c, g, or t

<400> SEQUENCE: 1

| | | | | | |
|---|---|---|---|---|---|
| ttggaaaaca | aaagttattg | tagttagttt | tgcttcttgc | gtgtccagcc | agcaaaatgg | 60 |
| gtgccggtgg | taggatgcca | attgacggta | taaaggagga | aaatcgaggc | tcggtcaatc | 120 |
| gagttccgat | cgagaagcct | ccgtttacgc | tcggtcagat | caagcaagcc | attccgcccc | 180 |
| actgttttcg | ccgctccctc | cttcgatcct | tctcctacgt | ggtccatgac | ctatgcttag | 240 |
| cctctctctt | ttactacatt | gcaacatcat | attttcactt | cctcccacaa | ccctttcct | 300 |
| acattgcttg | gcctgtctat | tgggttctcc | aaggttgcat | cctcaccggt | gtttgggtca | 360 |
| tcgcacacga | atgcggtcac | cacgctttca | gtgactacca | atgggttgac | gacaccgtcg | 420 |
| ggttgatcct | tcactccgcc | cttttagtcc | cgtacttctc | gtggaaaatc | agtcaccgcc | 480 |
| gtcaccactc | gaacaccggt | tccatggagc | gtgacgaagt | attcgtgccc | aaacccaagt | 540 |
| ctaaattatc | atgctttgcg | aaatacttca | acaatccacc | cggtcgagtt | ctctctcttg | 600 |
| tagtcacatt | gactcttggt | tggcatatgt | acttagcctt | caacgtttcg | ggtcgatact | 660 |
| atgatcgatt | agcttcccac | tataacccatt | acggccccat | ttactccgaa | cgcgagaggc | 720 |
| tacaagttta | catctccgat | gctggtatag | ttgcggtaat | ttatgtactt | tataagattg | 780 |
| ctgcaacaaa | agggctggct | tggcttttat | gcacttatgg | ggtacctcta | cttattgtga | 840 |
| atgccttcct | tgtgttgatc | acctacttgc | aacatactca | ctcggcattg | ccgcattacg | 900 |
| actcgtctga | atgggattgg | tttcgaggag | cattgtcgac | gattgatcga | gattacgggg | 960 |
| tgttgaacaa | agtgttccat | aacatcaccg | atacgcatgt | ggctcatcac | ctcttctcaa | 1020 |
| cgatgccaca | ttatcatgca | atggaggcca | ctaaagcaat | caaaccgata | ctcggcaagt | 1080 |
| attatccttt | cgacgggaca | ccgatttata | aggcaatgtg | gagggaggca | aaagagtgcc | 1140 |
| tttacgtcga | ggctgacgtt | ggtggtggtg | gtagctgtta | agaaatggct | taaaattggt | 1200 |
| agtggattgt | tgttgttggt | agtggggttgt | tggtggtagt | ggattagtgg | atggttgttg | 1260 |
| gtgtccattt | tcaaccacaa | atctttgcca | aagttttgga | caattatgtc | cttgaactct | 1320 |
| cttataaata | gagaggttca | ttagccatat | tcatcatccc | aaaccaagag | agagcaaagc | 1380 |
| ttgttctttg | aaagctagga | ttttagcttt | cgggttttct | ataggggttg | agagttgtga | 1440 |
| ggttctcggg | ttgtgtcttg | agtgtaaaac | acttgtaatc | ttcatcttgt | tatagtgaaa | 1500 |
| tttcttttcg | cctctgcccg | tggacgtagg | cattaaagcc | gaaccacgta | aatccttgtg | 1560 |
| ttcactttat | ttttcgtttc | ggtcaattta | cttgtagtca | tatcggagtt | ctcgaatcga | 1620 |
| tcctttccgc | aacaaattgg | tatcagagcg | tagttgaagg | agtgataata | ttttctgaat | 1680 |
| tgccctgtga | ctgcagcttt | gtctgatctt | tcacatcagg | aagaaantat | tatcattcat | 1740 |
| tcaaaggttc | caaattatgg | ctacaag | | | | 1767 |

<210> SEQ ID NO 2
<211> LENGTH: 89
<212> TYPE: DNA
<213> ORGANISM: Gossypium barbadense (Accession GB0331)

<400> SEQUENCE: 2

```
tgttaagaaa tggcttaaaa ttggtagtgg attgttgttg ttggtagtgg gttgttggtg    60
gtagtggatt agtggatggt tgttggtgt                                      89
```

<210> SEQ ID NO 3
<211> LENGTH: 374
<212> TYPE: PRT
<213> ORGANISM: Gossypium barbadense (Accession GB0331)

<400> SEQUENCE: 3

```
Met Gly Ala Gly Gly Arg Met Pro Ile Asp Gly Ile Lys Glu Glu Asn
1               5                   10                  15

Arg Gly Ser Val Asn Arg Val Pro Ile Glu Lys Pro Pro Phe Thr Leu
            20                  25                  30

Gly Gln Ile Lys Gln Ala Ile Pro Pro His Cys Phe Arg Arg Ser Leu
        35                  40                  45

Leu Arg Ser Phe Ser Tyr Val Val His Asp Leu Cys Leu Ala Ser Leu
    50                  55                  60

Phe Tyr Tyr Ile Ala Thr Ser Tyr Phe His Phe Leu Pro Gln Pro Phe
65                  70                  75                  80

Ser Tyr Ile Ala Trp Pro Val Tyr Trp Val Leu Gln Gly Cys Ile Leu
                85                  90                  95

Thr Gly Val Trp Val Ile Ala His Glu Cys Gly His His Ala Phe Ser
            100                 105                 110

Asp Tyr Gln Trp Val Asp Asp Thr Val Gly Leu Ile Leu His Ser Ala
        115                 120                 125

Leu Leu Val Pro Tyr Phe Ser Trp Lys Ile Ser His Arg Arg His His
    130                 135                 140

Ser Asn Thr Gly Ser Met Glu Arg Asp Glu Val Phe Val Pro Lys Pro
145                 150                 155                 160

Lys Ser Lys Leu Ser Cys Phe Ala Lys Tyr Phe Asn Asn Pro Pro Gly
                165                 170                 175

Arg Val Leu Ser Leu Val Val Thr Leu Thr Leu Gly Trp His Met Tyr
            180                 185                 190

Leu Ala Phe Asn Val Ser Gly Arg Tyr Tyr Asp Arg Leu Ala Ser His
        195                 200                 205

Tyr Asn Pro Tyr Gly Pro Ile Tyr Ser Glu Arg Glu Arg Leu Gln Val
    210                 215                 220

Tyr Ile Ser Asp Ala Gly Ile Val Ala Val Ile Tyr Val Leu Tyr Lys
225                 230                 235                 240

Ile Ala Ala Thr Lys Gly Leu Ala Trp Leu Leu Cys Thr Tyr Gly Val
                245                 250                 255

Pro Leu Leu Ile Val Asn Ala Phe Leu Val Leu Ile Thr Tyr Leu Gln
            260                 265                 270

His Thr His Ser Ala Leu Pro His Tyr Asp Ser Ser Glu Trp Asp Trp
        275                 280                 285

Phe Arg Gly Ala Leu Ser Thr Ile Asp Arg Asp Tyr Gly Val Leu Asn
    290                 295                 300

Lys Val Phe His Asn Ile Thr Asp Thr His Val Ala His His Leu Phe
305                 310                 315                 320

Ser Thr Met Pro His Tyr His Ala Met Glu Ala Thr Lys Ala Ile Lys
                325                 330                 335

Pro Ile Leu Gly Lys Tyr Tyr Pro Phe Asp Gly Thr Pro Ile Tyr Lys
```

Ala Met Trp Arg Glu Ala Lys Glu Cys Leu Tyr Val Glu Ala Asp Val
         340                 345                 350
Gly Gly Gly Gly Ser Cys
    355                 360                 365
370

<210> SEQ ID NO 4
<211> LENGTH: 383
<212> TYPE: PRT
<213> ORGANISM: Gossypium raimondii

<400> SEQUENCE: 4

Met Gly Ala Gly Gly Arg Met Pro Ile Asp Gly Ile Lys Glu Glu Asn
1               5                   10                  15

Arg Gly Ser Val Asn Arg Val Pro Ile Glu Lys Pro Pro Phe Thr Leu
            20                  25                  30

Gly Gln Ile Lys Gln Ala Ile Pro Pro His Cys Phe Arg Arg Ser Leu
        35                  40                  45

Leu Arg Ser Phe Ser Tyr Val Val His Asp Leu Cys Leu Ala Ser Leu
    50                  55                  60

Phe Tyr Tyr Ile Ala Ala Ser Tyr Phe His Phe Leu Pro Gln Pro Phe
65                  70                  75                  80

Ser Tyr Ile Ala Trp Pro Val Tyr Trp Val Leu Gln Gly Cys Ile Leu
                85                  90                  95

Thr Gly Val Trp Val Ile Ala His Glu Cys Gly His His Ala Phe Ser
            100                 105                 110

Asp Tyr Gln Trp Val Asp Asp Thr Val Gly Leu Ile Leu His Ser Ala
        115                 120                 125

Leu Leu Val Pro Tyr Phe Ser Trp Lys Ile Ser His Arg Arg His His
    130                 135                 140

Ser Asn Thr Gly Ser Met Glu Arg Asp Glu Val Phe Val Pro Lys Pro
145                 150                 155                 160

Lys Ser Lys Leu Ser Cys Phe Ala Lys Tyr Phe Asn Asn Pro Pro Gly
                165                 170                 175

Arg Val Leu Ser Leu Val Val Thr Leu Thr Leu Gly Trp Pro Met Tyr
            180                 185                 190

Leu Ala Phe Asn Val Ser Gly Arg Tyr Tyr Asp Arg Leu Ala Ser His
        195                 200                 205

Tyr Asn Pro Tyr Gly Pro Ile Tyr Ser Glu Arg Glu Arg Leu Gln Val
    210                 215                 220

Tyr Ile Ser Asp Ala Gly Ile Val Ala Val Ile Tyr Val Leu Tyr Lys
225                 230                 235                 240

Ile Ala Ala Thr Lys Gly Leu Ala Trp Leu Leu Cys Thr Tyr Gly Val
                245                 250                 255

Pro Leu Leu Ile Val Asn Ala Phe Leu Val Leu Ile Thr Tyr Leu Gln
            260                 265                 270

His Thr His Ser Ala Leu Pro His Tyr Asp Ser Ser Glu Trp Asp Trp
        275                 280                 285

Phe Arg Gly Ala Leu Ser Thr Ile Asp Arg Asp Tyr Gly Val Leu Asn
    290                 295                 300

Lys Val Phe His Asn Ile Thr Asp Thr His Val Ala His His Leu Phe
305                 310                 315                 320

Ser Thr Met Pro His Tyr His Ala Met Glu Ala Thr Lys Ala Ile Lys
                325                 330                 335

```
Pro Ile Leu Gly Lys Tyr Tyr Pro Phe Asp Gly Thr Pro Ile Tyr Lys
            340                 345                 350

Ala Met Trp Arg Glu Ala Lys Glu Cys Leu Tyr Val Glu Ala Asp Val
        355                 360                 365

Gly Gly Gly Gly Ser Lys Gly Val Phe Trp Tyr Arg Asn Lys Phe
    370                 375                 380

<210> SEQ ID NO 5
<211> LENGTH: 23
<212> TYPE: DNA
<213> ORGANISM: Artificial Sequence
<220> FEATURE:
<223> OTHER INFORMATION: Primer 1

<400> SEQUENCE: 5
ttggaaaaca aaagttattg tag                                         23

<210> SEQ ID NO 6
<211> LENGTH: 27
<212> TYPE: DNA
<213> ORGANISM: Artificial Sequence
<220> FEATURE:
<223> OTHER INFORMATION: Primer 2, reverse sequence

<400> SEQUENCE: 6
ttaattatga ttataatcca tgtactc                                     27

<210> SEQ ID NO 7
<211> LENGTH: 27
<212> TYPE: DNA
<213> ORGANISM: Artificial Sequence
<220> FEATURE:
<223> OTHER INFORMATION: Primer 2, complement

<400> SEQUENCE: 7
gagtacatgg attataatca taattaa                                     27

<210> SEQ ID NO 8
<211> LENGTH: 24
<212> TYPE: DNA
<213> ORGANISM: Artificial Sequence
<220> FEATURE:
<223> OTHER INFORMATION: Primer 3, reverse sequence

<400> SEQUENCE: 8
aactctcaac ccctatagaa aacc                                        24

<210> SEQ ID NO 9
<211> LENGTH: 24
<212> TYPE: DNA
<213> ORGANISM: Artificial Sequence
<220> FEATURE:
<223> OTHER INFORMATION: Primer 3, complement

<400> SEQUENCE: 9
ggttttctat aggggttgag agtt                                        24

<210> SEQ ID NO 10
<211> LENGTH: 1759
<212> TYPE: DNA
<213> ORGANISM: Gossypium barbadense (PIMA S6)
<220> FEATURE:
<221> NAME/KEY: misc_feature
<222> LOCATION: (1615)..(1615)
<223> OTHER INFORMATION: n is a, c, g, or t
```

<400> SEQUENCE: 10

```
gcatgctcga gcggccgcca gtgtgatgga tatctgcaga attcgccctt ttggaaaaca      60
aaagttattg tagttagttt tgcttcttgc gtgtccagcc agcaaaatgg atgccggtgg     120
taggatgcca attgacggta taaaggagga aaatcgaggc tcggtcaatc gagttccgat     180
cgagaagcct ccgtttacgc tcggtcagat caagcaagcc attccgcccc actgttttcg     240
ccgctccctc cttcgatcct tctcctacgt ggtccatgac ctatgcttag cctctctctt     300
ttactacatc gcaacatcat attttcactt tctcccacaa ccctttttcct acattgcttg    360
gcctgtctat tgggttctcc aaggttgcat cctcaccggt gtttgggtca tcgcacacga     420
atgcggtcac cacgctttca gtgactacca atgggttgac gacaccgtcg ggttgatcct     480
tcactccgcc cttttagtcc cgtacttctc gtggaaaatc agtcaccgcc gtcaccactc     540
gaacaccggt tccatggagc gtgacgaagt attcgtgccc aaacccaagt ctaaattatc     600
atgctttgcg aaatacttca caatccaccc cggtcgagtt ctctctcttg tagtcacatt     660
gactcttggt tggcatatgt acttagcctt caacgtttcg ggtcgatact atgatcgatt     720
agcttcccac tataacccct acggccccat ttactccgaa cgcgagaggc tacaagttta     780
catctccgat gctggtatag ttgcggtaat ttatgtactt taagattg ctgcaacaaa      840
agggctggct tggcttttat gcacttatgg ggtacctcta cttattgtga atgccttcct     900
tgtgctgatc acctacttgc aacatactca ctcggcattg ccgcattacg actcgtctga     960
atgggattgg tttcgaggag cattgtcgac gattgatcga gattacgggg tgttgaacaa    1020
agtgttccat aacatcaccg atacgcatgt ggctcatcac ctcttctcaa cgatgccaca    1080
ttatcatgca atggaggcca ctaaagcaat caaaccgata ctcggcaagt attatccttt    1140
cgacgggaca ccgatttata aggcaatgtg gagggaggca aaagagtgcc tttacgtcga    1200
ggctgacgtt ggtggtggtg gtagcaaagg tgttttttgg tatcgtaaca agttctaaag    1260
acagaccaac tgcctgatag ctggccggca aaatcgacgt aaaacgtact tattagacta    1320
gtgttaacta gggaagttaa taatggtagg aaaatgtgga atagctgcct agtagtttta    1380
tgtattaagt gttatattaa taaactatat ggtagaaaaa aaaatgtgca agtgctataa    1440
tgttttatgg acgctactaa aatagatcaa agattaaatt ttagatgcac aaagagtaca    1500
tggattataa tcataattaa acttaaattt atttggtgtt ggttcactca ctttggatcg    1560
cccaaaggtt gtttcatcat catttattga actcagttgt ttcaaaatta aaaanttata    1620
aactaaaact cgactcaaga tgaatcgaat tgcttgatta aaccaactca actcagtcta    1680
tttttgagca atttagtatt ttcaactttta cgctggtctg atcagaccga tttactatta    1740
aatgactaaa aaatataaa                                                 1759
```

<210> SEQ ID NO 11
<211> LENGTH: 1776
<212> TYPE: DNA
<213> ORGANISM: Gossypium barbadense (Accession GB0331)

<400> SEQUENCE: 11

```
ctagatgcat gctcgagcgg ccgccagtgt gatggatatc tgcagaattc gcccttttgg     60
aaaacaaaag ttattgtagt tagttttgct tcttgcgtgt ccagccagca aatgggtgc     120
cggtggtagg atgccaattg acggtataaa ggaggaaaat cgaggctcgg tcaatcgagt    180
tccgatcgag aagcctccgt ttacgctcgg tcagatcaag caagccattc cgccccactg    240
ttttcgccgc tccctccttc gatccttctc ctacgtggtc catgacctat gcttagcctc    300
```

-continued

```
tctcttttac tacattgcaa catcatattt tcacttcctc ccacaaccct tttcctacat    360
tgcttggcct gtctattggg ttctccaagg ttgcatcctc accggtgttt gggtcatcgc    420
acacgaatgc ggtcaccacg ctttcagtga ctaccaatgg gttgacgaca ccgtcgggtt    480
gatccttcac tccgcccttt tagtcccgta cttctcgtgg aaaatcagtc accgccgtca    540
ccactcgaac accggttcca tggagcgtga cgaagtattc gtgcccaaac ccaagtctaa    600
attatcatgc tttgcgaaat acttcaacaa tccacccggt cgagttctct ctcttgtagt    660
cacattgact cttggttggc atatgtactt agccttcaac gtttcgggtc gatactatga    720
tcgattagct tcccactata acccttacgg ccccatttac tccgaacgcg agaggctaca    780
agtttacatc tccgatgctg gtatagttgc ggtaatttat gtactttata agattgctgc    840
aacaaaaggg ctggcttggc ttttatgcac ttatggggta cctctactta ttgtgaatgc    900
cttccttgtg ttgatcacct acttgcaaca tactcactcg gcattgccgc attacgactc    960
gtctgaatgg gattggtttc gaggagcatt gtcgacgatt gatcgagatt acggggtgtt   1020
gaacaaagtg ttccataaca tcaccgatac gcatgtggct catcacctct tctcaacgat   1080
gccacattat catgcaatgg aggccactaa agcaatcaaa ccgatactcg gcaagtatta   1140
tcctttcgac gggacaccga tttataaggc aatgtggagg gaggcaaaag agtgccttta   1200
cgtcgaggct gacgttggtg gtggtggtag ctgttaagaa atggcttaaa attggtagtg   1260
gattgttgtt gttggtagtg ggttgttggt ggtagtggat tagtggatgg ttgttggtgt   1320
ccattttcaa ccacaaatct ttgccaaagt tttggacaat tatgtccttg aactctctta   1380
taaatagaga ggttcattag ccatattcat catcccaaac caagagagag caaagcttgt   1440
tctttgaaag ctaggatttt agctttcggg ttttctatag gggttgagag ttgtgaggtt   1500
ctcgggttgt gtcttgagtg taaaacactt gtaatcttca tcttgttata gtgaaatttc   1560
ttttcgcctc tgcccgtgga cgtaggcatt aaagccgaac cacgtaaatc cttgtgttca   1620
ctttattttt cgtttcggtc aatttacttg tagtcatatc ggagttctcg aatcgatcct   1680
ttccgcaaca aattggtatc agagcgtagt tgaaggagtg ataatatttt ctgaattgcc   1740
ctgtgactgc agctttgtct gatctttcac atcagg                             1776
```

HIGH OLEIC SEED OIL TRAIT IN COTTON VARIETIES TO ELEVATE OLEIC ACID CONTENT OF COTTONSEED OIL

This application claims priority to U.S. Provisional Patent Application Serial No. 62/355,064, entitled "High Oleic Seed Oil Trait in Cotton Varieties to Elevate Oleic Acid Content of Cottonseed Oil," filed on Jun. 27, 2016, the entire contents of which are hereby incorporated by reference.

BACKGROUND

This disclosure pertains to elevation of oleic acid content of commercial cottonseed oil using a non-GMO (genetically modified organism) strategy. This disclosure also relates to the identification of a high oleic seed variant and its use in monitoring the introgression of a naturally-occurring high oleic seed oil trait into cotton varieties, including Pima and upland cotton varieties.

Although cotton is farmed for its production of spinnable fibers, the residual seed after ginning is an important global source of vegetable oil. In fact, the yield of seed on a per acre basis is about 1.6 times that of the harvested fiber, and in 2012 this amounted to 5.37 million tons of cottonseed produced in the United States (USDA-Oil Crops Outlook). Currently less than half of the seed produced in the United States is crushed and processed into refined vegetable oil, and with world demand for vegetable oils on the rise, this represents a place for farmers to recognize additional value from their overall crop. Oilseeds and their refined vegetable oils vary in price based on their compositional formulations and end use markets. Due to its oxidative stability and flavor enhancing properties, cottonseed oil enjoys a reputation as an excellent frying oil, but with changes to its fatty acid composition, cottonseed oil might enter other markets (Lui et al., 2009; 2012). As with all natural products, the compositions of extracted products may vary from season to season, with environmental and genetic factors contributing to both desirable and undesirable components.

A more complete understanding of the many components in refined cottonseed oils and the factors which influence their formation within the embryo, may help to develop new varieties with consistent and highly desirable vegetable oil compositions. Detailed chemical analysis of seed oils (including minor components) within the context of different genotypes or environmental conditions could help to provide breeders with rich resources to enhance the overall value of the cotton crop. Moreover, the detailed analysis of lipid metabolites within embryos may offer insights into pathways and postharvest processes that influence seed viability and seedling vigor.

Vegetable oils are a major source of calories in most western diets, and their nutritional and physical properties are dependent upon their fatty acid composition. Important for improved oxidative stability is a reduced level of unsaturation, and until recently this was accomplished largely by the chemical hydrogenation of most vegetable oils. However, by-products of hydrogenation are trans-fatty acids and due to health concerns about these non-natural fats, other options for reduced polyunsaturated oils have been sought. Most desirable have been the development of crop varieties that produced seeds with high oleic oils, or enhanced mono-unsaturate-containing oils, as these oils have perceived health benefits and exceptional stability in frying applications. Most oilseed crops have now been developed with high oleic seed varieties through transgenic and/or non-transgenic means. With concerns expressed by some consumers about foods harboring so-called genetically modified organisms (GMO), and the lengthy, expensive prospects of de-regulating transgenic traits, there has been a keen interest to develop crops with altered seed oil compositions through breeding approaches rather than through targeted, transgenic techniques. The success of the breeding approach relies, in part, on an existing variant gene pool with diversity in the seed fatty acid composition. While there is considerable variation in fatty acid composition found in the genetic backgrounds of most major oilseed crops, upland cotton (*Gossypium hirsutum*, L.) has been reported to exhibit a rather narrow range in seed oleic acid content (~15-20% of the total fatty acid composition) when large germplasm collections have been examined (Liu et al., 2009).

SUMMARY

The present disclosure relates generally to identification and tracking of a naturally-occurring high oleic seed oil trait in cotton varieties.

In particular, a wild accession of *Gossypium barbadense* (Accession GB0331, from the National Cotton Germplasm Collection) with a high oleic seed oil phenotype was identified. This accession has high oil content and an increased percentage of oleic acid in the triacylglycerols (TAGs) in the seeds, the principal component of refined cottonseed oil. This high oleic acid content in the seed TAGs was correlated with increased oleic acid content in the phosphatidylcholines (PC) of the seed, the metabolic precursor to acyl groups incorporated into the TAGs. A mutation was identified in the genome of GB0331 within the D-homeologue of the seed-specific fatty acid desaturase (FAD2-1) that is responsible for converting oleic acid to linoleic acid while it is esterified to PC. A 90 base pair insertion in the GB0331 genome disrupted the coding sequence of the FAD2-1D near the 3' end of the protein coding region which resulted in a predicted polypeptide truncated at the C-terminus. This 90 bp sequence was not found in reference genomes of other *Gossypium* species, especially that of adapted varieties of *G. barbadense* and *G. hirsutum*, indicating that this DNA segment will be useful to track the high oleic fad-2-1D mutant allele for introgression into cotton varieties such as Pima and upland cotton varieties. This enables a non-GMO strategy to elevate the oleic acid content of commercial cottonseed oil.

The enzymes and corresponding genes for polyunsaturated fatty acid biosynthesis in plants have been well studied, and the major rate limiting step in the conversion of oleic acid to linoleic acid in seeds is the delta-12 fatty acid desaturase (FAD2, also known as the omega-6 desaturase). While the model plant *Arabidopsis thaliana* has a single FAD2 gene, most oilseed crops have a seed specific isoform of FAD2 (e.g., soybean FAD2-1) that is highly expressed in seed tissues and is responsible for linoleic acid production in developing seeds. The FAD2-1 isoform was identified in cotton by Liu et al. (2009), and it has been subsequently confirmed by gene specific suppression strategies that a targeted reduction in FAD2-1 expression in transgenic cotton plants can result in high oleic acid cottonseeds (reviewed in Liu et al., 2009).

The present disclosure takes an entirely different approach. Following up on a large-scale germplasm screen for genetic variation of seed oil and protein content (Hinze et al., 2014), attention was focused on selected genotypes with dramatic differences in seed oil-to-protein ratios. A detailed examination of the lipid compositions of the seeds of one wild *Gossypium* accession (*G. barbadense*, accession GB0331) revealed high oleic acid (~45% by weight) relative to conventional, commercial upland cotton (*G. hirsutum;* ~15% by weight) or Pima cottons (*G. barbadense;* ~22% by weight) seed fatty acids. It has been demonstrated that a wild accession of *Gossypium barbadense*, L (Pima cotton) harbors a mutant allele of the D-genome homeologue of FAD2-1, and that this disrupted allele is associated with a high oleic acid seed phenotype. Neither a wild accession collected from a nearby geographical location, nor the commercially bred *G. barbadense* cultivar, Pima S6, harbored this exact chromosomal segment and both had normal levels of seed oleic acid. Because both upland and pima cotton species are allotetraploids with both and A and D genome, this D-genome allele represents a genetic element that can be readily crossed into adapted varieties for commercialization of a non-GMO, high-oleic cottonseed oil in long staple, Pima varieties, or short staple, upland varieties.

DETAILED DESCRIPTION OF PREFERRED EMBODIMENTS

Generally, the present disclosure relates to a method for simple and accurate tracking of a high oleic trait in cotton varieties. The trait is tracked by identifying a natural genetic mutant allele containing 90-base pair insertion in the seed-specific FAD2-1D gene during introgression by polymerase chain reaction or other nucleotide sequence detection methods. This enables a breeding strategy to elevate oleic acid in commercial, refined cottonseed oil that does not rely on GMO transgenic technologies.

In preferred embodiments, the present disclosure relates to generating cotton seeds having an elevated oleic acid content, in which the cotton plants have been identified as having a high oleic acid trait. A first step may include obtaining a cotton plant suspected of having a high oleic acid trait. Next steps may include extracting nucleic acid material from cells of the cotton plant, then amplifying the nucleic acid material extracted from cells of the cotton plant using a primer. The primer preferably comprises a sequence that is specific for the 90-base pair insertion in the mutated FAD2-1D allele that is found in the cotton plant genome. A next step may be detecting amplified mutated nucleic acid material from cells of the cotton plant, wherein detection of amplified mutated nucleic acid material identifies the cotton plant as having a high oleic acid trait. The cotton plant identified as having a high oleic acid trait may then be used to generate cotton seeds, wherein the cotton seeds have an elevated oleic acid content.

Preferably, the cotton plant is obtained through at least one act of cross-breeding of parental generation cotton plants. This may be a single cross-breeding or multiple cross-breedings involving multiple parental generations. At least a portion of the parental generation cotton plants may lack a high oleic acid trait while at least another portion of the parental generation cotton plants should include a high oleic acid trait as well as a genome having the insertion in the mutated FAD2-1D allele. The insertion in the mutated FAD2-1D allele comprises SEQ ID NO:2 in preferred embodiments. While any primer targeting this insertion (SEQ ID NO:2) can be used, preferred embodiments may utilize a primer comprising SEQ ID NO:8.

In additional embodiments, a second primer may be used which targets a sequence absent from the mutated FAD2-1D allele found in the cotton plant genome. If no amplified nucleic acid material is detecting using this second primer, this also means the mutation is present in the cotton plant's genome, meaning the cotton plant can be identified as having a high oleic acid trait. In certain preferred embodiments, this second primer comprises SEQ ID NO:6.

In additional preferred embodiments, the cotton plant identified as having a high oleic acid trait may be cross-bred with additional cotton plants that may lack a high oleic acid trait. In further preferred embodiments, a cotton seed may be suspected of having a high oleic acid trait and the steps of extracting and amplifying nucleic acid may be carried out using the seed. If the cotton seed is identified as having a high oleic acid trait, it may be germinated into a cotton plant having a high oleic acid trait, and this cotton plant may be cross-bred with other cotton plants lacking a high oleic acid trait.

EXAMPLE 1

Comparison of Seed Oil Amounts

Table 1 below shows how selected varieties of seed from diverse *Gossypium* genotypes and species have different amounts of seed oil. Table 1 shows a comparison of seed size, % oil (by weight), % protein (by weight) for selected *Gossypium* accessions representing a broad range of oil and protein content across diverse genomes in the U.S. National Cotton Germplasm Collection. Oil and protein content were determined by TD-NMR in triplicate batches of seeds at approximately 1 g each. Values are means and standard deviations.

TABLE 1

| Sample ID | Species | Genome/ Race | Distribution | Seed Size (mg/seed) | Oil (%) | Protein (%) |
|---|---|---|---|---|---|---|
| B01-1 | *G. anomalum* | B1 | Africa | 24.4 | 12.8 ± 0.3 | 20.2 ± 0.3 |
| D01-10 | *G. thurberi* | D1 | Mexico/Arizona | 21.0 | 16.6 ± 0.3 | 11.4 ± 0.3 |
| E01-3 | *G. stocksii* | E1 | Arabia | 24.1 | 8.2 ± 0.3 | 23.8 ± 0.3 |
| GB-0331 | *G. barbadense* | (AD)2 | South America | 116.7 | 26.2 ± 0.6 | 27.3 ± 0.8 |

TABLE 1-continued

| Sample ID | Species | Genome/ Race | Distribution | Seed Size (mg/seed) | Oil (%) | Protein (%) |
|---|---|---|---|---|---|---|
| PIMA-6 | G. barbadense | (AD)2 | South America | 119.2 | 25.5 ± 0.3 | 16.3 ± 0.4 |
| SA-1254 | G. hirsutum | (AD)1 | Central/North America | 98.7 | 20.0 ± 0.4 | 37.4 ± 2.1 |
| TX-2236 | G. hirsutum | (AD)1 | Central/North America | 59.5 | 14.4 ± 0.1 | 31.0 ± 0.4 |
| TX-2500 | G. hirsutum | (AD)1 | Central/North America | 90.2 | 24.8 ± 0.1 | 23.0 ± 0.5 |
| Coker 312 | G. hirsutum | (AD)1 | Central/North America | 83.9 | 20.6 ± 0.3 | 24.0 ± 1.5 |

EXAMPLE 2

Seed Triacylglycerols

Figure 1:
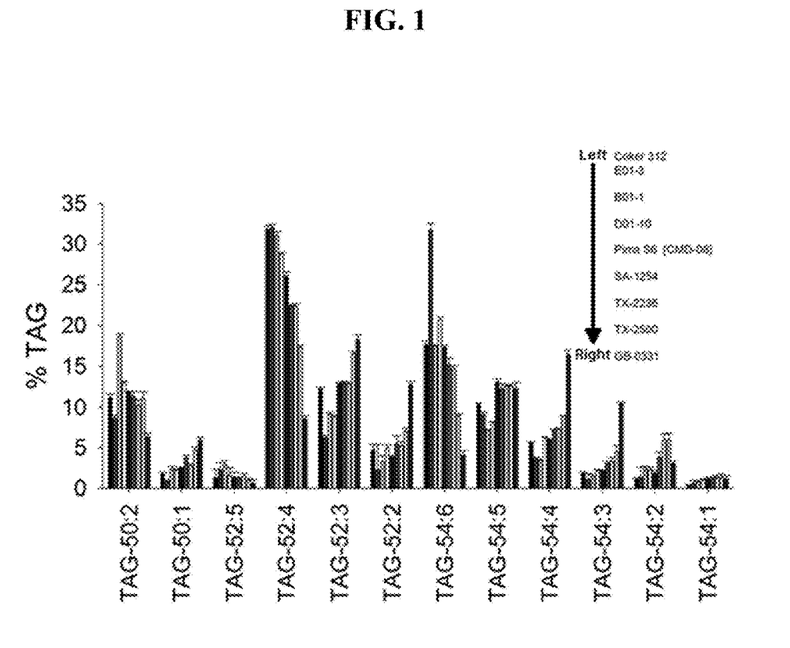
FIG. 1 shows a comparison of amounts of different molecular species of triacylglycerols (TAGs) found in total seed lipid extracts from nine *Gossypium* genotypes.

Seed triacylglycerols (TAGs) of GB0331 are enriched in oleic acid, compared to other diverse genotypes and species. FIG. 1 shows different molecular species of triacylglycerols (TAGs) found in total seed lipid extracts from nine Gossypium genotypes (see Table 1). The numerical designation indicates total number of carbons in all three acyl chains: total number of double bonds. Thus, TAG 54:3 has 3 oleic acids, TAG 54:4 has two oleic acids TAG 52:2 has two oleic acids. The relative quantification of TAG species are presented on a mol % basis within the class and were measured in triplicate with 5 seeds each in each replicate. Bars represent standard deviation. Tandem MS scanning mode confirmed acyl chain composition. The nine genotypes are shown for each TAG molecular species with Coker 312 at the left and GB-0331 at the right and the others in between as shown in the figure. As seen in FIG. 1, TAG 54:3, TAG 54:4 and TAG 52:2, all containing oleic acid, are higher in GB0331 than other genotypes.

EXAMPLE 3

Seed Phosphatidylcholines

Figure 2:
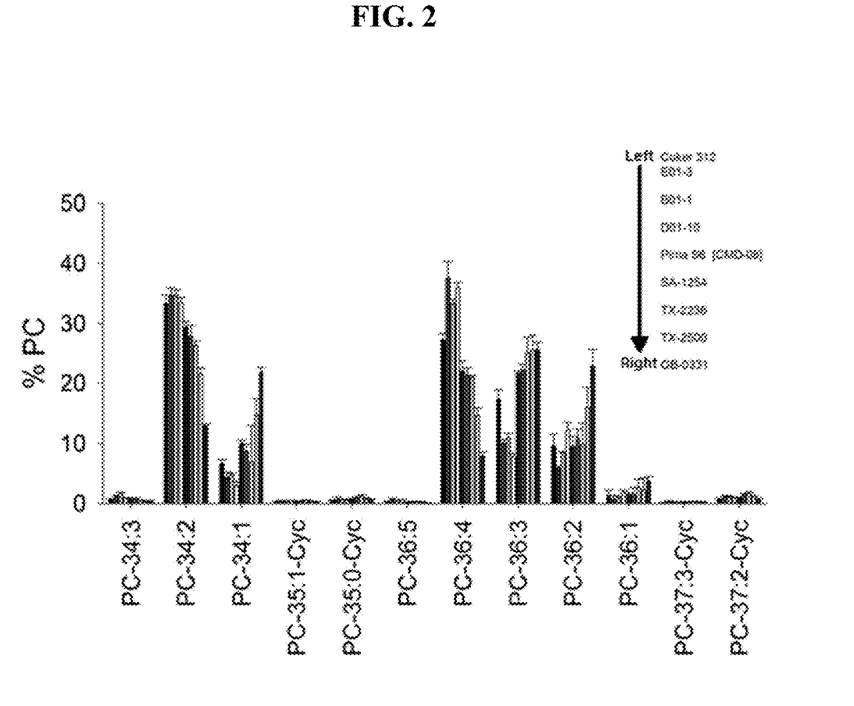
FIG. 2 shows a comparison of amounts of different molecular species of phosphatidylcholines (PCs) found in total seed lipid extracts from nine *Gossypium* genotypes.

Seed phosphatidylcholines (PCs) of GB0331 are enriched in oleic acid, compared to other diverse genotypes and species. FIG. 2 shows the molecular species of phosphatidylcholines (PCs) found in total seed lipid extracts from nine Gossypium genotypes (see Table 1). The numerical designation indicates total number of carbons in both acyl chains: total number of double bonds. Cyc indicates the presence of a cyclopropane or cyclopropane ring in one acyl chain, and these Cyc-containing species were minor contributors to the total PC pool. Relative quantification of PC species is presented on a mol % basis within the class and was measured in triplicate with 5 seeds each in each replicate. The bars represent standard deviation. Tandem MS scanning mode confirmed acyl chain composition. The nine genotypes are shown for each molecular species with Coker 312 at the left and GB-0331 at the right and the others in between as shown in the figure. As seen in FIG. 2, PC 34:1 and PC 36:2, both containing oleic acid, are higher in GB0331 than other genotypes.

EXAMPLE 4

Nucleotide Sequence

Below is the nucleotide sequence of the FAD2-1D allele from the GB0331 genome. A unique chromosomal variation, 90 nucleotide insertion (underlined), is present in the GB0331 genome and is not in any of the other Gossypium species genome sequences curated at Cottongen.org including the reference genome for G. barbadense. The sequence after that (not underlined) is conserved in all genomes as is the FAD2-1D sequence itself (the sequence beginning at base 57 and continuing up to the underlined sequence).

(SEQ ID NO: 1)
TTGGAAAACAAAAGTTATTGTAGTTAGTTTTGCTTCTTGCGTGTCCAGC

CAGCAAAATGGGTGCCGGTGGTAGGATGCCAATTGACGGTATAAAGGAG

GAAAATCGAGGCTCGGTCAATCGAGTTCCGATCGAGAAGCCTCCGTTTA

CGCTCGGTCAGATCAAGCAAGCCATTCCGCCCCACTGTTTTCGCCGCTC

CCTCCTTCGATCCTTCTCCTACGTGGTCCATGACCTATGCTTAGCCTCT

CTCTTTTACTACATTGCAACATCATATTTTCACTTCCTCCCACAACCCT

TTTCCTACATTGCTTGGCCTGTCTATTGGGTTCTCCAAGGTTGCATCCT

CACCGGTGTTTGGGTCATCGCACACGAATGCGGTCACCACGCTTTCAGT

GACTACCAATGGGTTGACGACACCGTCGGGTTGATCCTTCACTCCGCCC

TTTTAGTCCCGTACTTCTCGTGGAAAATCAGTCACCGCCGTCACCACTC

GAACACCGGTTCCATGGAGCGTGACGAAGTATTCGTGCCCAAACCCAAG

TCTAAATTATCATGCTTTGCGAAATACTTCAACAATCCACCCGGTCGAG

TTCTCTCTCTTGTAGTCACATTGACTCTTGGTTGGCATATGTACTTAGC

CTTCAACGTTTCGGGTCGATACTATGATCGATTAGCTTCCCACTATAAC

CCTTACGGCCCCATTTACTCCGAACGCGAGAGGCTACAAGTTTACATCT

CCGATGCTGGTATAGTTGCGGTAATTTATGTACTTTATAAGATTGCTGC

AACAAAAGGGCTGGCTTGGCTTTTATGCACTTATGGGGTACCTCTACTT

ATTGTGAATGCCTTCCTTGTGTTGATCACCTACTTGCAACATACTCACT

CGGCATTGCCGCATTACGACTCGTCTGAATGGGATTGGTTTCGAGGAGC

ATTGTCGACGATTGATCGAGATTACGGGGTGTTGAACAAAGTGTTCCAT

AACATCACCGATACGCATGTGGCTCATCACCTCTTCTCAACGATGCCAC

ATTATCATGCAATGGAGGCCACTAAAGCAATCAAACCGATACTCGGCAA

GTATTATCCTTTCGACGGGACACCGATTTATAAGGCAATGTGGAGGGAG

GCAAAAGAGTGCCTTTACGTCGAGGCTGACGTTGGTGGTGGTGGTAGC<u>T</u>

<u>GTTAAGAAATGGCTTAAAATTGGTAGTGGATTGTTGTTGTTGGTAGTGG</u>

<u>GTTGTTGGTGGTAGTGGATTAGTGGATGGTTGTTGGTGT</u>CCATTTTCAA

CCACAAATCTTTGCCAAAGTTTTGGACAATTATGTCCTTGAACTCTCTT

-continued

ATAAATAGAGAGGTTCATTAGCCATATTCATCATCCCAAACCAAGAGAG

AGCAAAGCTTGTTCTTTGAAAGCTAGGATTTTAGCTTTCGGGTTTTCTA

TAGGGGTTGAGAGTTGTGAGGTTCTCGGGTTGTGTCTTGAGTGTAAAAC

ACTTGTAATCTTCATCTTGTTATAGTGAAATTTCTTTTCGCCTCTGCCC

GTGGACGTAGGCATTAAAGCCGAACCACGTAAATCCTTGTGTTCACTTT

ATTTTTCGTTTCGGTCAATTTACTTGTAGTCATATCGGAGTTCTCGAAT

CGATCCTTTCCGCAACAAATTGGTATCAGAGCGTAGTTGAAGGAGTGAT

AATATTTTCTGAATTGCCCTGTGACTGCAGCTTTGTCTGATCTTTCACA

TCAGGAAGAAANTATTATCATTCATTCAAAGGTTCCAAATTATGGCTAC

AAG

Underlined sequence:
(SEQ ID NO: 2)
TGTTAAGAAATGGCTTAAAATTGGTAGTGGATTGTTGTTGTTGGTAGTG

GGTTGTTGGTGGTAGTGGATTAGTGGATGGTTGTTGGTGT

EXAMPLE 5

Amino Acid Sequence

As shown below, the deduced amino acid sequence of GB0331 FAD2-1D is shorter by about 10 amino acids (underlined portion) than that of the D-genome containing *Gossypium raimondii* (Gorai.013G248800) from which the *G. barbadense* lineage was likely derived.

GB0331 FAD2-1D deduced AA Sequence
(SEQ ID NO: 3)
MGAGGRMPIDGIKEENRGSVNRVPIEKPPFTLGQIKQAIPPHCFRRSLL

RSFSYVVHDLCLASLFYYIATSYFHFLPQPFSYIAWPVYWVLQGCILIG

VWVIAHECGHHAFSDYQWVDDTVGLILHSALLVPYFSWKISHRRHHSNI

GSMERDEVFVPKPKSKLSCFAKYFNNPPGRVLSLVVILTLGWHMYLAFN

VSGRYYDRLASHYNPYGPIYSERERLQVYISDAGIVAVIYVLYKIAATK

GLAWLLCTYGVPLLIVNAFLVLITYLQHTHSALPHYDSSEWDWFRGALS

TIDRDYGVLNKVFHNITDTHVAHHLFSIMPHYHAMEATKAIKPILGKYY

PFDGIPIYKAMWREAKECLYVEADVGGGGSC-

Gorai.013G248800 (FAD2-1D) deduced AA Reference Sequence
(SEQ ID NO: 4)
MGAGGRMPIDGIKEENRGSVNRVPIEKPPFTLGQIKQAIPPHCFRRSLL

RSFSYVVHDLCLASLFYYIAASYFHFLPQPFSYIAWPVYWVLQGCILIG

VWVIAHECGHHAFSDYQWVDDTVGLILHSALLVPYFSWKISHRRHHSNI

GSMERDEVFVPKPKSKLSCFAKYFNNPPGRVLSLVVILTLGWPMYLAFN

VSGRYYDRLASHYNPYGPIYSERERLQVYISDAGIVAVIYVLYKIAATK

GLAWLLCTYGVPLLIVNAFLVLITYLQHTHSALPHYDSSEWDWFRGALS

TIDRDYGVLNKVFHNITDTHVAHHLFSIMPHYHAMEATKAIKPILGKYY

PFDGIPIYKAMWREAKECLYVEADVGGGGS<u>KGVFWYRNKF</u>

This insertion results in a premature stop codon in the FAD2-1D from GB0331 such that the C-terminus of the predicted poly peptide is about 10 amino acids shorter than the normal FAD2-1D from other *Gossypium* genotypes with normal oleic acid. This region of the protein is responsible for its correct subcellular location in plant cells, and so even if was expressed, the protein would not localize to the endoplasmic reticulum where FAD2 encounters its substrate. Hence, the capacity for total FAD2 activity in GB0331 is reduced relative to "wildtype," leading to a high oleic content in PC and in the seed TAGs.

Figure 3:
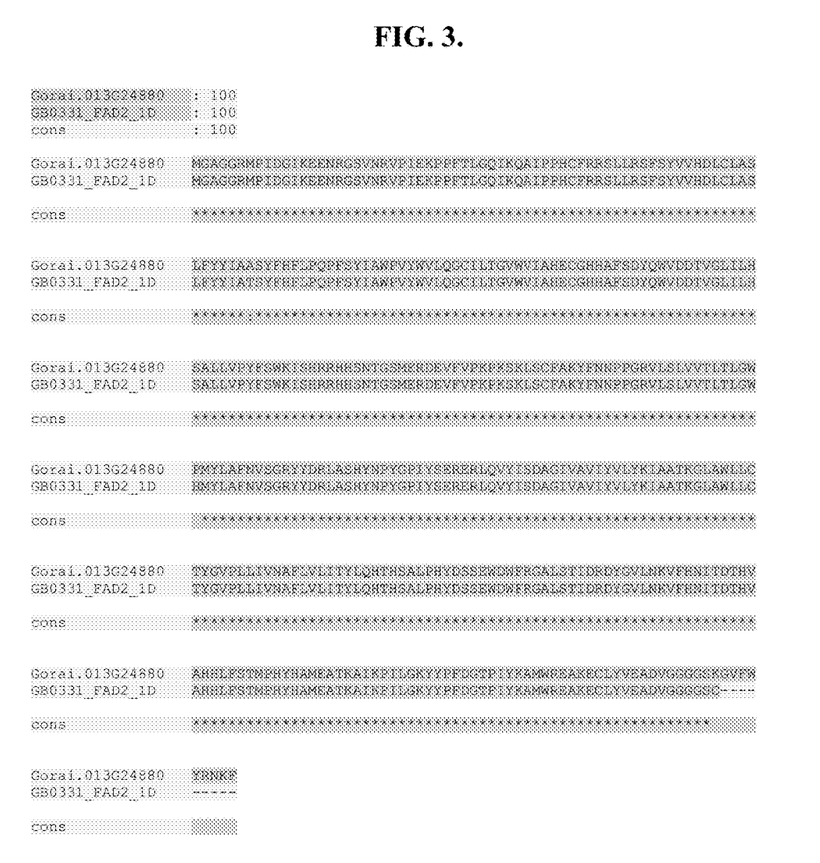
FIG. 3 shows an alignment of deduced amino acid sequence from the nucleotide sequence obtained from the FAD2-1D homeologue in GB0331 (SEQ ID NO:3), compared to the nucleotide sequence obtained from the FAD2-1D of *G. raimondii* (SEQ ID NO:4) performed by pairwise BLAST.

FIG. 3 shows an alignment of deduced amino acid sequence from the nucleotide sequence obtained from the FAD2-1D homeologue in GB0331, compared the FAD2-1D of *G. raimondii* performed by pairwise BLAST.

EXAMPLE 6

Amplification

A sequence-specific primer (primer 3) for the mutated allele only amplifies a DNA fragment from genomic DNA of GB0331, and not from the genomic DNA of accession GB0332 or PIMA S6. Conversely, a primer specific for the 3' end of the "normal", full-length FAD2-1 (primer 2), does not amplify a DNA fragment from the genomic DNA of GB0331, but does amplify bands from GB0332 and PIMA S6 with normal seed oleic acid content. The inserted DNA disrupts the "normal" sequence found in GB0331, hence a primer directed to this region cannot bind and amplify a DNA band. Actin primers amplify a predicted sized DNA fragment in all genomic DNA samples, serving as a control for the amplification of genomic DNA in all genotypes. Primer positions are underlined in two representative FAD2-1 sequences, one for the mutant GB0331, and one for the normal PIMA S6.

Primer 1 (forward sequence, underlined):
(SEQ ID NO: 5)
TTGGAAAACAAAAGTTATTGTAG

Primer 2 (Reverse) sequence (specific for normal FAD2-1D):
(SEQ ID NO: 6)
TTAATTATGATTATAATCCATGTACTC Primer 2 (complement, underlined):
(SEQ ID NO: 7)
GAGTACATGGATTATAATCATAATTAA Primer 3 (Reverse) sequence (specific for mutated FAD2-1D sequence):
(SEQ ID NO: 8)
AACTCTCAACCCCTATAGAAAACC Primer 3 (complement, underlined):
(SEQ ID NO: 9)
GGTTTTCTATAGGGGTTGAGAGTT

PIMA S6
(SEQ ID NO: 10)
GCATGCTCGAGCGGCCGCCAGTGTGATGGATATCTGCAGAATTCGCCCT

<u>TTTGGAAAACAAAAGTTATTGTAG</u>TTAGTTTTGCTTCTTGCGTGTCCAG

CCAGCAAAATGGATGCCGGTGGTAGGATGCCAATTGACGGTATAAAGGA

GGAAAATCGAGGCTCGGTCAATCGAGTTCCGATCGAGAAGCCTCCGTTT

ACGCTCGGTCAGATCAAGCAAGCCATTCCGCCCCACTGTTTTCGCCGCT

CCCTCCTTCGATCCTTCTCCTACGTGGTCCATGACCTATGCTTAGCCTC

TCTCTTTTACTACATCGCAACATCATATTTTCACTTTCTCCCACAACCC

-continued
TTTTCCTACATTGCTTGGCCTGTCTATTGGGTTCTCCAAGGTTGCATCC

TCACCGGTGTTTGGGTCATCGCACACGAATGCGGTCACCACGCTTTCAG

TGACTACCAATGGGTTGACGACACCGTCGGGTTGATCCTTCACTCCGCC

CTTTTAGTCCCGTACTTCTCGTGGAAAATCAGTCACCGCCGTCACCACT

CGAACACCGGTTCCATGGAGCGTGACGAAGTATTCGTGCCCAAACCCAA

GTCTAAATTATCATGCTTTGCGAAATACTTCAACAATCCACCCGGTCGA

GTTCTCTCTCTTGTAGTCACATTGACTCTTGGTTGGCATATGTACTTAG

CCTTCAACGTTTCGGGTCGATACTATGATCGATTAGCTTCCCACTATAA

CCCTTACGGCCCCATTTACTCCGAACGCGAGAGGCTACAAGTTTACATC

TCCGATGCTGGTATAGTTGCGGTAATTTATGTACTTTATAAGATTGCTG

CAACAAAAGGGCTGGCTTGGCTTTTATGCACTTATGGGGTACCTCTACT

TATTGTGAATGCCTTCCTTGTGCTGATCACCTACTTGCAACATACTCAC

TCGGCATTGCCGCATTACGACTCGTCTGAATGGGATTGGTTTCGAGGAG

CATTGTCGACGATTGATCGAGATTACGGGGTGTTGAACAAAGTGTTCCA

TAACATCACCGATACGCATGTGGCTCATCACCTCTTCTCAACGATGCCA

CATTATCATGCAATGGAGGCCACTAAAGCAATCAAACCGATACTCGGCA

AGTATTATCCTTTCGACGGGACACCGATTTATAAGGCAATGTGGAGGGA

GGCAAAAGAGTGCCTTTACGTCGAGGCTGACGTTGGTGGTGGTAGC

AAAGGTGTTTTTTGGTATCGTAACAAGTTCTAAAGACAGACCAACTGCC

TGATAGCTGGCCGGCAAAATCGACGTAAAACGTACTTATTAGACTAGTG

TTAACTAGGGAAGTTAATAATGGTAGGAAAATGTGGAATAGCTGCCTAG

TAGTTTTATGTATTAAGTGTTATATTAATAAACTATATGGTAGAAAAAA

AAATGTGCAAGTGCTATAATGTTTTATGGACGCTACTAAAATAGATCAA

AGATTAAATTTTAGATGCACAAA<u>GAGTACATGGATTATAATCATAATTA</u>

<u>A</u>ACTTAAATTTATTTGGTGTTGGTTCACTCACTTTGGATCGCCCAAAGG

TTGTTTCATCATCATTTATTGAACTCAGTTGTTTCAAAATTAAAAANTT

ATAAACTAAAACTCGACTCAAGATGAATCGAATTGCTTGATTAAACCAA

CTCAACTCAGTCTATTTTTGAGCAATTTAGTATTTTCAACTTTACGCTG

GTCTGATCAGACCGATTTACTATTAAATGACTAAAAAATATAAA

GB0331
                                                (SEQ ID NO: 11)
CTAGATGCATGCTCGAGCGGCCGCCAGTGTGATGGATATCTGCAGAATT

CGCCCTT<u>TTGAAAACAAAAGTTATTGTAG</u>TTAGTTTTGCTTCTTGCGT

GTCCAGCCAGCAAAATGGGTGCCGGTGGTAGGATGCCAATTGACGGTAT

AAAGGAGGAAATCGAGGCTCGGTCAATCGAGTTCCGATCGAGAAGCCT

CCGTTTACGCTCGGTCAGATCAAGCAAGCCATTCCGCCCACTGTTTTC

GCCGCTCCCTCCTTCGATCCTTCTCCTACGTGGTCCATGACCTATGCTT

AGCCTCTCTCTTTTACTACATTGCAACATCATATTTTCACTTCCTCCCA

CAACCCTTTTCCTACATTGCTTGGCCTGTCTATTGGGTTCTCCAAGGTT

GCATCCTCACCGGTGTTTGGGTCATCGCACACGAATGCGGTCACCACGC

TTTCAGTGACTACCAATGGGTTGACGACACCGTCGGGTTGATCCTTCAC

TCCGCCCTTTTAGTCCCGTACTTCTCGTGGAAAATCAGTCACCGCCGTC

ACCACTCGAACACCGGTTCCATGGAGCGTGACGAAGTATTCGTGCCCAA

ACCCAAGTCTAAATTATCATGCTTTGCGAAATACTTCAACAATCCACCC

GGTCGAGTTCTCTCTCTTGTAGTCACATTGACTCTTGGTTGGCATATGT

ACTTAGCCTTCAACGTTTCGGGTCGATACTATGATCGATTAGCTTCCCA

CTATAACCCTTACGGCCCCATTTACTCCGAACGCGAGAGGCTACAAGTT

TACATCTCCGATGCTGGTATAGTTGCGGTAATTTATGTACTTTATAAGA

TTGCTGCAACAAAAGGGCTGGCTTGGCTTTTATGCACTTATGGGGTACC

TCTACTTATTGTGAATGCCTTCCTTGTGTTGATCACCTACTTGCAACAT

ACTCACTCGGCATTGCCGCATTACGACTCGTCTGAATGGGATTGGTTTC

GAGGAGCATTGTCGACGATTGATCGAGATTACGGGGTGTTGAACAAAGT

GTTCCATAACATCACCGATACGCATGTGGCTCATCACCTCTTCTCAACG

ATGCCACATTATCATGCAATGGAGGCCACTAAAGCAATCAAACCGATAC

TCGGCAAGTATTATCCTTTCGACGGGACACCGATTTATAAGGCAATGTG

GAGGGAGGCAAAAGAGTGCCTTTACGTCGAGGCTGACGTTGGTGGTGGT

GGTAGCTGTTAAGAAATGGCTTAAAATTGGTAGTGGATTGTTGTTGTTG

GTAGTGGGTTGTTGGTGGTAGTGGATTAGTGGATGGTTGTTGGTGTCCA

TTTTCAACCACAAATCTTTGCCAAAGTTTTGGACAATTATGTCCTTGAA

CTCTCTTATAAATAGAGAGGTTCATTAGCCATATTCATCATCCCAAACC

AAGAGAGAGCAAAGCTTGTTCTTTGAAAGCTAGGATTTTAGCTTTCG<u>GG</u>

<u>TTTTCTATAGGGGTTGAGAGTTGT</u>GAGGTTCTCGGGTTGTGTCTTGAGT

GTAAAACACTTGTAATCTTCATCTTGTTATAGTGAAATTTCTTTTCGCC

TCTGCCCGTGGACGTAGGCATTAAAGCCGAACCACGTAAATCCTTGTGT

TCACTTTATTTTTCGTTTCGGTCAATTTACTTGTAGTCATATCGGAGTT

CTCGAATCGATCCTTTCCGCAACAAATTGGTATCAGAGCGTAGTTGAAG

GAGTGATAATATTTTCTGAATTGCCCTGTGACTGCAGCTTTGTCTGATC

TTTCACATCAGG

Figure 4:
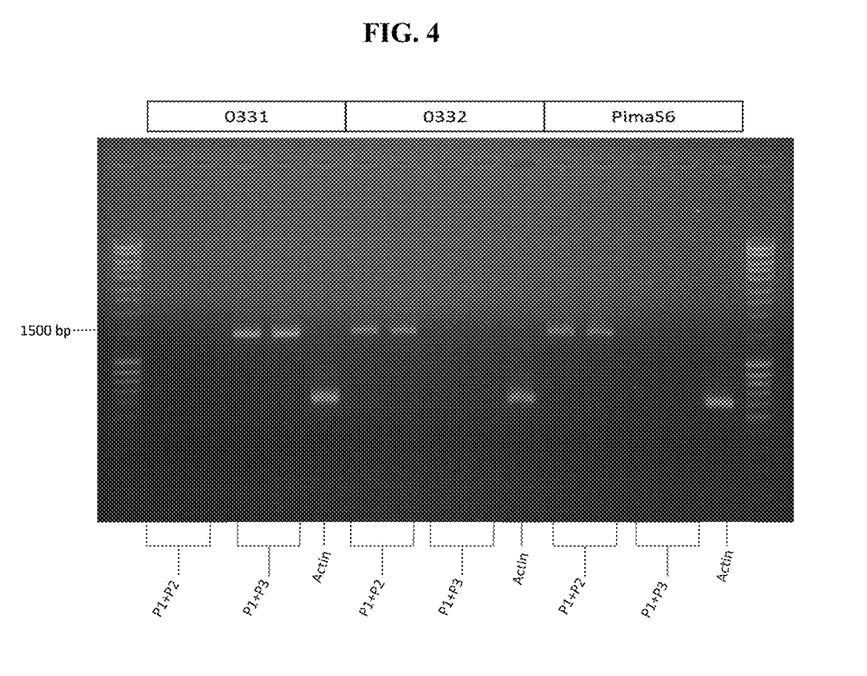
FIG. 4 shows agarose gel separation of FAD2-1D amplification products from genomic DNA of GB0331, GB0332 and PIMA S6 using different primers (P1, P2, and P3).

FIG. 4 shows agarose gel separation of FAD2-1D amplification products from genomic DNA of GB0331, GB0332 and PIMA S6. Primer sequence locations are described and shown above. P3 is specific for the mutated sequence in GB0331 that disrupts the C-terminus of FAD2-1D. It only amplifies a band in GB0331. P2 is specific for the "normal" 3' end of FAD2-1D. Results demonstrate that the FAD2-1D in GB0331 is different from that in the other *G. barbadense* genotypes within the sequence of the 3'end of the gene (see also example 4), and results in high oleic acid content in seeds.

What is claimed is:

1. A method for obtaining and identifying cotton seeds generated to have an elevated oleic acid content, comprising:
   obtaining a cotton plant suspected of having a high oleic acid trait;
   extracting nucleic acid material from cells of the cotton plant;
   amplifying the nucleic acid material extracted from cells of the cotton plant using a primer comprising a sequence specific for an insertion in a mutated FAD2-1D allele found in the cotton plant genome, wherein the insertion in the mutated FAD2-1D allele comprises SEQ ID NO:2;
   detecting amplified mutated nucleic acid material from cells of the cotton plant, wherein detection of amplified mutated nucleic acid material identifies the cotton plant as having a high oleic acid trait; and
   generating cotton seeds from the cotton plant, wherein the cotton seeds have an elevated oleic acid content.

2. The method of claim 1, wherein the cotton plant is obtained through at least one act of cross-breeding of parental generation cotton plants, wherein at least a portion of the parental generation cotton plants lack a high oleic acid trait and at least another portion of the parental generation cotton plants comprise a high oleic acid trait and a genome having the insertion in the mutated FAD2-1D allele.

3. The method of claim 1, wherein the primer comprises a sequence targeting the insertion in the mutated FAD2-1D allele comprising SEQ ID NO:2.

4. The method of claim 1, wherein the primer comprises SEQ ID NO:8.

5. The method of claim 1, wherein the step of amplifying the nucleic acid material extracted from cells of the cotton plant further comprises using a second primer targeting a sequence absent from the mutated FAD2-1D allele found in the cotton plant genome, wherein the second primer amplifies non-mutated nucleic acid material, and further comprising the step of detecting a lack of amplified non-mutated nucleic acid material wherein detection of a lack of amplified non-mutated nucleic acid material further identifies the cotton plant as having a high oleic acid trait.

6. The method of claim 5, wherein the second primer comprises SEQ ID NO:6.

7. The method of claim 1, further comprising the step of cross-breeding the cotton plant identified as having a high oleic acid trait with one or more cotton plants lacking a high oleic acid trait.

8. A method for obtaining and identifying a cotton plant having a high oleic acid trait, comprising:
   obtaining a cotton seed suspected of having a high oleic acid trait;
   extracting nucleic acid material from cells of the cotton seed;
   amplifying the nucleic acid material extracted from cells of the cotton seed using a primer comprising a sequence specific for an insertion in a mutated FAD2-1D allele found in the cotton seed genome, wherein the insertion in the mutated FAD2-1D allele comprises SEQ ID NO:2;
   detecting amplified mutated nucleic acid material from cells of the cotton seed, wherein detection of amplified mutated nucleic acid material identifies the cotton seed as having a high oleic acid trait; and
   germinating the cotton seed to produce a cotton plant, wherein the cotton plant has a high oleic acid trait.

9. The method of claim 8, wherein the cotton seed is obtained through at least one act of cross-breeding of parental generation cotton plants, wherein at least a portion of the parental generation cotton plants lack a high oleic acid trait and at least another portion of the parental generation cotton plants comprise a high oleic acid trait and a genome having the insertion in the mutated FAD2-1D allele.

10. The method of claim 8, wherein the primer comprises a sequence targeting the insertion in the mutated FAD2-1D allele comprising SEQ ID NO:2.

11. The method of claim 8, wherein the primer comprises SEQ ID NO:8.

12. The method of claim 8, wherein the step of amplifying the nucleic acid material extracted from cells of the cotton seed further comprises using a second primer targeting a sequence absent from the mutated FAD2-1D allele found in the cotton seed genome, wherein the second primer amplifies non-mutated nucleic acid material, and further comprising the step of detecting a lack of amplified non-mutated nucleic acid material wherein detection of a lack of amplified non-mutated nucleic acid material further identifies the cotton seed as having a high oleic acid trait.

13. The method of claim 12, wherein the second primer comprises SEQ ID NO:6.

14. The method of claim 8, further comprising the step of cross-breeding the cotton plant identified as having a high oleic acid trait with one or more cotton plants lacking a high oleic acid trait.

* * * * *